United States Patent
Lewis

(10) Patent No.: US 7,367,804 B2
(45) Date of Patent: May 6, 2008

(54) ENDODONTIC INSTRUMENT EXTRACTOR TOOL MANUFACTURED FROM A SHAPE MEMORY MATERIAL AND RELATED KITS AND METHODS

(75) Inventor: Paul Lewis, Midvale, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 11/467,418

(22) Filed: Aug. 25, 2006

(65) Prior Publication Data

US 2008/0050696 A1 Feb. 28, 2008

(51) Int. Cl.
*A61C 5/12* (2006.01)
*A61C 3/00* (2006.01)
*A61C 5/08* (2006.01)
*A61C 5/00* (2006.01)

(52) U.S. Cl. ............ 433/141; 433/139; 433/153; 433/163; 433/152; 433/220; 433/215; 433/127

(58) Field of Classification Search ............ 433/139, 433/141, 153, 163, 152, 220, 215, 244, 127, 433/21

See application file for complete search history.

(56) References Cited

U.S. PATENT DOCUMENTS

| | | | |
|---|---|---|---|
| 3,322,124 A | 5/1967 | Donald | 433/141 |
| 3,703,767 A | 11/1972 | Masserann et al. | 433/161 |
| 3,906,636 A | 9/1975 | Rainey | 433/102 |
| 4,337,038 A | 6/1982 | Saito et al. | 433/32 |
| 4,746,292 A | 5/1988 | Johnson | 433/141 |
| 5,879,160 A * | 3/1999 | Ruddle | 433/141 |
| 5,893,713 A | 4/1999 | Garman et al. | 433/32 |
| 5,915,964 A | 6/1999 | Walia | 433/102 |
| 6,227,855 B1 | 5/2001 | Hickok et al. | 433/141 |
| 6,494,713 B1 | 12/2002 | Pond | 433/81 |
| 6,575,748 B1 | 6/2003 | Filhol | 433/102 |
| 6,976,844 B2 | 12/2005 | Hickok et al. | 433/224 |
| 7,021,935 B2 | 4/2006 | Aeby et al. | 433/224 |
| 2003/0124485 A1 | 7/2003 | Teraushi | 433/141 |
| 2006/0286511 A1* | 12/2006 | Aleksandrovskiy et al. | 433/215 |
| 2007/0134621 A1* | 6/2007 | Terauchi | 433/102 |

FOREIGN PATENT DOCUMENTS

DE        1023195        11/2001

(Continued)

*Primary Examiner*—Sam Chuan Yao
*Assistant Examiner*—Yogesh P Patel
(74) *Attorney, Agent, or Firm*—Workman Nydegger

(57) ABSTRACT

An endodontic instrument extractor tool is configured for removing a fragment of a broken endodontic instrument that has become lodged within a root canal of a tooth. The extractor tool comprises an elongate shaft, including a hollow gripping body at a distal end, and a proximal handle portion. The hollow gripping body includes an inside diameter that is initially greater than a cross-sectional dimension of a fragment of a broken endodontic instrument to be removed from a root canal of a tooth. The inside diameter of the hollow gripping body defines a hollow interior cavity portion into which at least a portion of the fragment is receivable. At least the hollow gripping body of the body is formed of a shape memory alloy (e.g., nickel-titanium) or polymer in an expanded configuration so that upon heating, the shape memory alloy or polymer returns to its unexpanded configuration, tightly gripping around a proximal end of the fragment.

25 Claims, 8 Drawing Sheets

FOREIGN PATENT DOCUMENTS

| | | |
|---|---|---|
| EP | 1440668 | 7/2004 |
| JP | 01/269356 | 10/2001 |
| JP | 04/024621 | 1/2004 |
| JP | 05/160542 | 6/2005 |
| WO | WO 05/018477 | 3/2005 |
| WO | WO 05/077286 | 8/2005 |
| WO | WO 2005077286 A1 * | 8/2005 |

* cited by examiner

ENDODONTIC INSTRUMENT EXTRACTOR TOOL MANUFACTURED FROM A SHAPE MEMORY MATERIAL AND RELATED KITS AND METHODS

BACKGROUND OF THE INVENTION

1. The Field of the Invention

The present invention relates to procedures that employ endodontic instruments in preparing a root canal of a tooth for receiving a sealer and/or filler material. More particularly, the invention relates to devices, kits, and methods for removing a portion of an endodontic instrument that has broken off the main shaft and become lodged within the root canal being prepared.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material that forms the nerve of the tooth, which has become infected. After careful preparation of the canal that contained the nerve material, the canal is refilled with an inert filling material, such as gutta percha. This process allows the patient to retain the tooth.

To achieve a successful root canal restoration, the dental practitioner must carefully and, as completely as possible, remove the infected pulp material. The removal process typically includes shaping the root canal so that it can be effectively and successfully filled and sealed with an inert material to reduce the possibility of further infection.

Cleaning and shaping the root canal in preparation for receiving a sealing and/or filling material is achieved by the use of metal endodontic instruments that include cutting surfaces for removing tissue in the root canal. Since root canals are seldom straight, often having bends and twists, at least some endodontic instruments are flexible so as to allow the instrument to follow the curvature of the root canal. Currently preferred materials of construction include stainless steel and super-elastic alloys, e.g., some nickel-titanium (Ni-Ti) alloys. Although such instruments generally exhibit good flexibility, resilience, and strength, they can sometimes fail during use within a root canal of a tooth, resulting in a broken instrument fragment becoming tightly lodged within the root canal of a tooth.

The consequences of leaving and/or bypassing broken instrument fragments within the root canal can be serious. In some cases, leaving the broken instrument in the tooth can result in later complications that require extraction of the tooth. Because of this, it is generally preferred that the broken instrument be removed from the root canal, if possible, to prevent additional future problems. Still, it has generally been very difficult to remove broken instrument fragments. In particular, most broken instruments are files, drills, bores, or other cutting instruments that broke after becoming wedged inside the structure of the root. Therefore, the very fact that the instrument was broken generally indicates that the instrument became stuck in the tooth structure and could not be easily pulled free. In addition, the instrument often breaks at a point deep within the canal, not easily visible or accessible to the practitioner.

Until now, there has been a lack of simple, efficient, and effective means for removing the broken instrument fragment in order to complete the endodontic procedure, which would be advantageous as removal and subsequent filling and sealing the root canal would minimize the possibility of later infection and/or loss of the tooth. Therefore, what is needed is an extraction tool, related kit, and method that would facilitate simple, efficient, and effective removal of the broken instrument fragment from the root canal.

BRIEF SUMMARY OF THE PREFERRED EMBODIMENTS

In one aspect, the present invention is directed to an endodontic extractor tool for removing a broken endodontic instrument that has become lodged within a root canal of a tooth. The endodontic instrument extractor comprises an elongate shaft having a proximal end and a distal end, a hollow gripping body portion at the distal end, and a proximal handle portion. The hollow gripping body includes an inside diameter that is initially greater than a cross-sectional dimension (e.g., diameter) of a broken endodontic instrument to be removed from a root canal of a tooth. The inside diameter of the hollow gripping body defines a hollow interior portion into which at least a portion of the broken endodontic instrument can be received. At least the hollow gripping body of the device is formed of a shape memory alloy (e.g., nickel-titanium alloy, nickel-titanium-niobium, nickel-titanium-copper, copper-zinc-aluminum, or copper-aluminum-nickel) or shape memory polymer (e.g., VERIFLEX) in an expanded configuration. Upon heating, the shape memory alloy returns to its unexpanded configuration. In other words, the inside diameter of the hollow gripping body is reduced upon heating, which facilitates gripping around a proximal end of the broken endodontic instrument. Because the broken endodontic instrument is gripped very tightly within the hollow interior cavity portion of the extractor, it can be removed together with the endodontic instrument extractor by simply gripping the proximal handle portion and pulling and/or twisting both the extractor tool and the broken endodontic instrument from the root canal of the tooth.

A related kit includes an endodontic extractor tool as described above and an endodontic coring tool. The endodontic coring tool includes a body configured as a hollow cylindrical tube having a cutting surface formed at a distal end of the hollow tube. Often, the break in an endodontic instrument occurs deep within the root canal, such that no portion of the instrument fragment is exposed outside of the root canal. The endodontic coring tool of the inventive kit is helpful as it allows the practitioner to core around and expose a proximal end of the broken instrument fragment so that it can be removed with the extractor tool.

The inventive kit may advantageously include multiple endodontic extractor tools and/or multiple endodontic coring tools of different diameters. Such a kit allows a practitioner to select a tool or tools having a diameter corresponding to the cross-sectional dimension (e.g., diameter) of the broken instrument. For example, such a kit may include a first endodontic extractor tool having a first relatively small inside diameter that is configured for use in removing endodontic instrument fragments corresponding to a range of relatively small diameters. A second endodontic extractor tool includes a hollow gripping body having a second relatively larger inside diameter that is greater than the inside diameter of the first extractor tool such that the second endodontic extractor tool is specifically configured for use in removing broken endodontic instrument fragments falling within a range of relatively larger diameters. Such a kit may advantageously include three or more differently sized extractor tools (e.g., a first extractor tool configured for use with "small" diameter fragments, a second extractor tool configured for use with "medium" diameter fragments, and a third extractor tool configured for use in removing "large" diameter fragments). Similarly, included endodontic coring tools may be included in a plurality of sizes for coring around and exposing a proximal end of broken instrument fragments of various diameters.

According to a related method for removing a portion of a broken endodontic instrument lodged within a root canal, a practitioner selects an appropriately sized endodontic extractor tool having an initial inside diameter that corresponds to a diameter of a broken endodontic instrument that is wedged and/or lodged within the root canal of the tooth. If needed, an endodontic coring tool may be used to clean out and core around a proximal end of the broken endodontic instrument so as to expose a length of the proximal end of the broken endodontic instrument fragment. The hollow gripping body of the endodontic extractor tool is then inserted into the root canal such that at least an end of the broken endodontic instrument is received within the cavity defined by the hollow gripping body of the endodontic extractor tool. The selected extractor tool advantageously includes an initial inside diameter within the hollow interior portion that is larger than the diameter of the broken endodontic instrument fragment, which allows the proximal end of the instrument fragment to be easily received within the hollow gripping body.

Once in place, at least the hollow gripping body of the endodontic extractor tool is heated (e.g., by electrical resistance heating, or even by body heat) so as to cause the shape memory alloy or polymer of the hollow gripping body to return to an unexpanded configuration. In other words, the inside diameter of the hollow gripping body is reduced upon heating so as to grip the portion of the broken endodontic instrument fragment that is received within the cavity of the endodontic extractor tool. The return of the shape memory alloy or polymer to an unexpanded configuration results in a very tight grip between the hollow gripping body and the broken instrument fragment. Because the extractor tool is able to tightly grip the instrument fragment, the extractor tool and the gripped instrument fragment may then be pulled and/or twisted out so as to remove both the extractor tool and the broken instrument fragment from the root canal of the tooth. The irregular cutting surface of the endodontic instrument fragment advantageously increased the friction, and hence, the grip, between the file fragment and the extractor tool.

The practitioner may then proceed to complete the endodontic procedure (e.g., cleaning, filling, and sealing of the root canal) that was being performed when the endodontic instrument became broken and lodged within the root canal. The inventive extractor tool, kit, and method advantageously provide a simple and effective way for a practitioner to remove broken endodontic instrument fragments that have become lodged within the root canal of a tooth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1A:
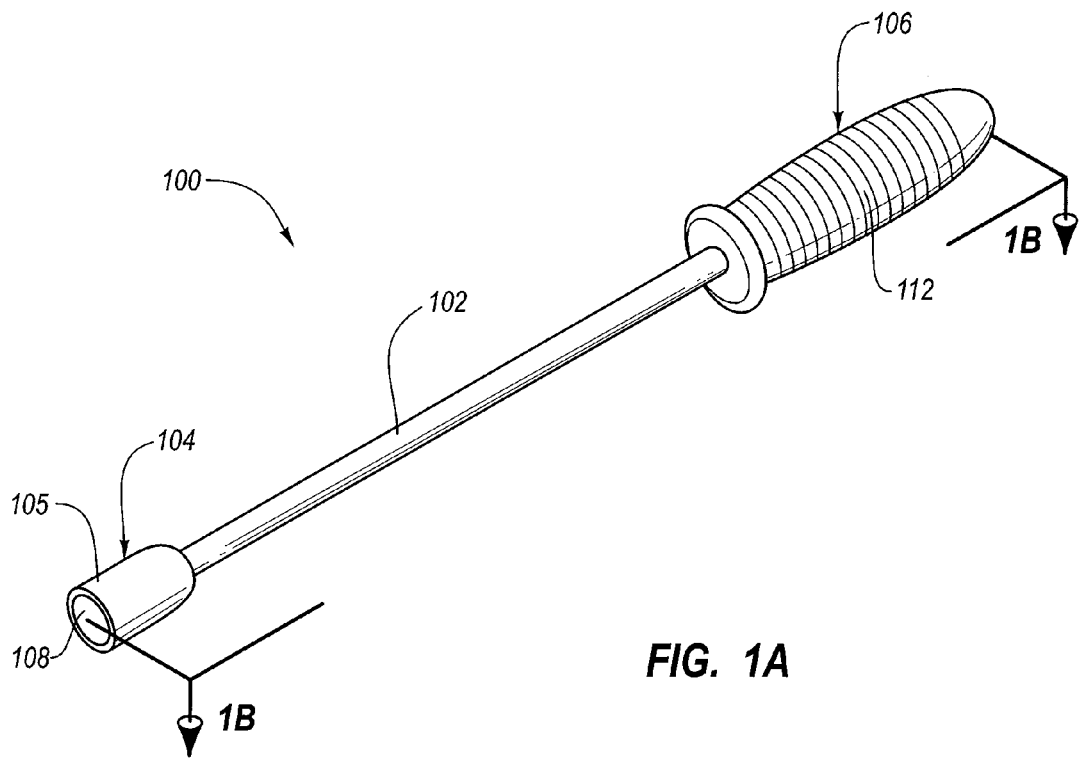
FIG. 1A is a perspective view of an exemplary endodontic instrument extractor tool in an expanded configuration.

In one aspect, the present invention is directed to an endodontic extractor tool for removing a broken endodontic instrument that has become lodged within a root canal of a tooth. The endodontic instrument extractor tool comprises an elongate shaft having a proximal end and a distal end, a hollow gripping body at a distal end, and a proximal handle portion. The hollow gripping body includes an inside diameter that is initially greater than a cross-sectional dimension (i.e., diameter) of a broken endodontic instrument fragment to be removed from a root canal of a tooth. The inside diameter of the hollow gripping body defines a hollow interior portion into which at least a portion of the broken endodontic instrument fragment is receivable. The term "diameter" is used for convenience in describing the cross-sectional dimension of a broken endodontic fragment, although it is to be understood that such fragments may have cross-sectional shapes other than round, such that "diameter" is to be construed broadly to encompass cross-sectional dimensions of other shapes (e.g., triangular, rectangular, etc.).

At least the hollow gripping body is formed of a shape memory material (e.g., an alloy or polymer) in an expanded configuration. In other words, during manufacture, the hollow gripping body is physically deformed so as to stretch, deform, and expand the hollow interior cavity portion of the hollow gripping body. Such a procedure is typically performed at room temperature or below (e.g., about 0° F. to about 70° F.) during manufacture of the extractor tool. The cavity maintains this deformed and expanded configuration until heated to a given higher temperature, which triggers a transformation that causes the material to return to its original, pre-expanded configuration.

Upon heating (e.g., by electrical resistance heating or even exposure to body heat), the shape memory alloy or polymer returns to an unexpanded configuration such that the inside diameter of the gripping body is reduced, which facilitates gripping around an end of a broken endodontic instrument fragment. The use of such means to grip the broken endodontic instrument fragment results in a very tight grip, and advantageously does not have any moving parts and does not require any manipulation by the practitioner to grip or otherwise hold an end of the instrument fragment (other than simply positioning the hollow gripping body over at least part of the broken instrument fragment, and then heating the shape memory alloy or polymer to cause it to tightly grip the instrument fragment). Because the broken endodontic instrument is gripped very tightly it can be removed together with the endodontic instrument extractor by simply gripping the proximal handle portion at the proximal end of the elongate shaft and pulling both the extractor and the broken endodontic instrument fragment from the root canal of the tooth. The roughened surface of a cutting portion of a endodontic file further increases the grip between a broken fragment and the extractor tool.

II. Exemplary Endodontic Extractor Tools and Related Kits

Figure 1B:
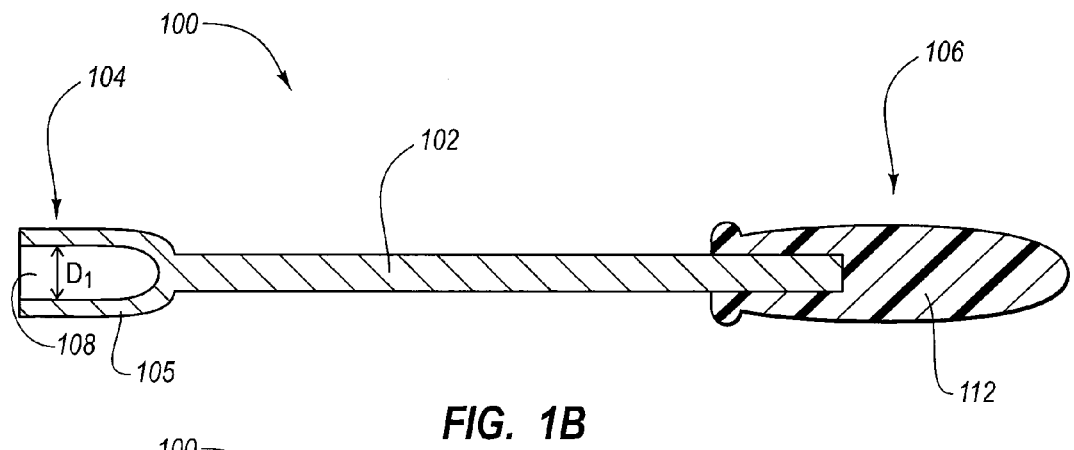
FIG. 1B is a cross-sectional view of the extractor tool of FIG. 1A.
Figure 1C:
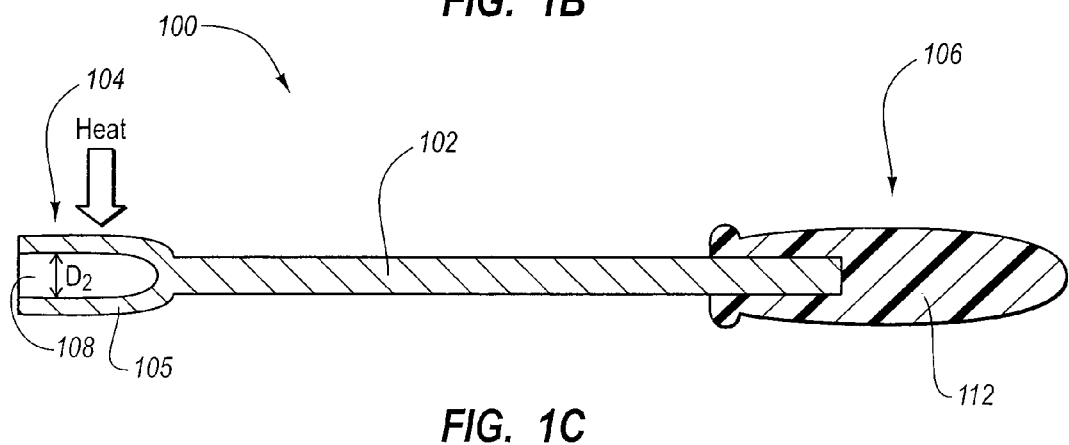
FIG. 1C is a cross-sectional view of the extractor tool of FIGS. 1A-1B, after the shape memory alloy of the hollow gripping body has been heated so as to return to an unexpanded configuration.

FIGS. 1A-1C illustrate an exemplary endodontic instrument extractor tool 100, which includes an elongate shaft 102 having a proximal end and distal end, a hollow gripping body 104 at the distal end, and a gripping portion 106 at the proximal end. Elongate shaft 102 has a length so that the proximal end extends outside the tooth when the distal end is positioned within a root canal of a tooth. FIGS. 1A-1B illustrate tool 100 where hollow gripping body 104 is in an expanded configuration, while FIG. 1C illustrates the same tool 100 after heating has caused the hollow gripping body 104 to assume a smaller diameter $D_2$. Referring to FIGS. 1A-1B, hollow gripping body 104 is, for example, bell-shaped so as to have an outer wall that is outwardly flared. The interior surface of outer wall 105 defines a hollow interior portion 108 having an initial inside diameter $D_1$. Initial diameter $D_1$ is advantageously configured to be slightly larger than the diameter of a broken endodontic instrument fragment. Exemplary initial inside diameters $D_1$ range from about 0.03 mm to about 1.75 mm. The gripping body 104 can alternatively be substantially cylindrical without significant flaring of an outer wall thereof. The term "diameter" is used for convenience in describing the cross-sectional dimension within the hollow interior portion 108 defined by outer wall 105. Although so used, it is to be understood that the hollow interior portion may have cross-sectional shapes other than round, such that "diameter" is to be construed broadly to encompass cross-sectional dimensions of other shapes (e.g., triangular, rectangular, etc.).

The interior surface of hollow interior portion 108 may advantageously be substantially smooth, which may simplify manufacture of the tool as no additional machining to create intentional undercuts or roughening of the interior surface is required. Even with a substantially smooth interior surface, the hollow gripping body 104 is able to grip a fragment of a broken endodontic instrument very tightly because of the action of the shape memory alloy or polymer and the friction imparted by the broken file fragment itself. Alternatively, the interior surface of the gripping body 104 may itself be roughed to increase friction with an endodontic file (e.g., having a smooth shaft, such as an apical file).

As illustrated, proximal gripping portion 106 includes a structure that can be gripped by the practitioner (e.g., a handle 112 configured to be gripped by the hand of a practitioner or an end (not shown) configured for insertion and gripping within a dental hand piece). The handle 112 may advantageously comprise a flexible, elastomeric material to enhance grip.

Gripping body 104 is characterized as being in an initially expanded configuration. Such an expansion may be accomplished during manufacture by physically deforming and expanding hollow interior portion 108 of gripping body 104 so as to expand its initial internal diameter $D_1$. For example, a mandrel or other steel tool may be inserted into cavity 108 under force so as to expand the cavity. In other words, cavity 108 may originally have a diameter equal to $D_2$ as shown in FIG. 1C, which is expanded under force during manufacture so as to assume a configuration where the inside diameter is equal to $D_1$, as shown in FIGS. 1A-1B.

The expansion of the inside diameter of cavity 108 is performed at a temperature less than that required to cause the shape memory alloy or polymer to return to an unexpanded configuration. For example, such a procedure may be performed at a temperature between about 0° F. and about room temperature (e.g., about 70° F.), while a temperature of at least about body temperature (e.g., about 100° F.) or above is advantageously required to cause the shape memory alloy or polymer to return to an unexpanded configuration.

At least the gripping body 104 of extractor tool 100 is formed of a shape memory alloy or polymer. According to one currently preferred embodiment, the gripping body 104 comprises a nickel-titanium alloy having shape memory. The selected nickel-titanium alloy preferably comprises at least about 40% titanium, more preferably at least about 45% titanium, and most preferably at least about 50% titanium (e.g., about 52% titanium). The balance of the alloy may consist essentially of nickel. In another embodiment it may include at least one of copper and/or niobium in addition to nickel. Examples of suitable shape memory Ni-Ti alloys include, but are not limited to various alloys sold by MEMORY-METALLE GMBH including ALLOY M, ALLOY B, ALLOY H, and FLEXINOL WIRE.

Figure 2A:
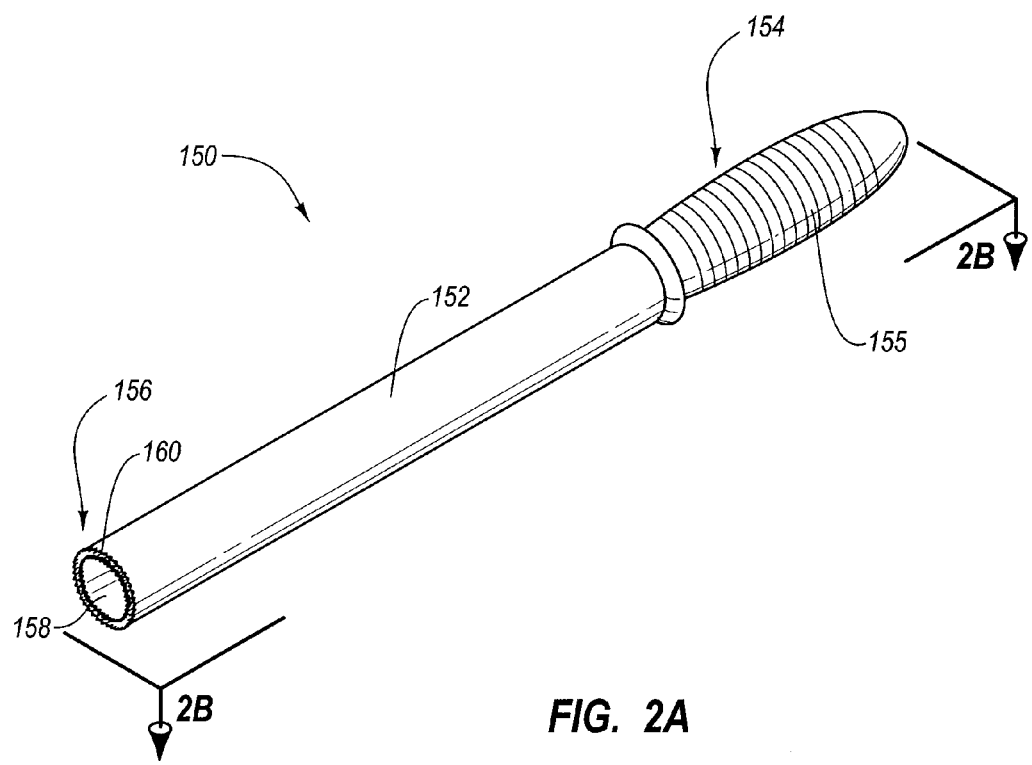
FIG. 2A is a perspective view of an exemplary endodontic coring tool for use in a kit with the extractor tool of FIGS. 1A-1B.
Figure 2B:
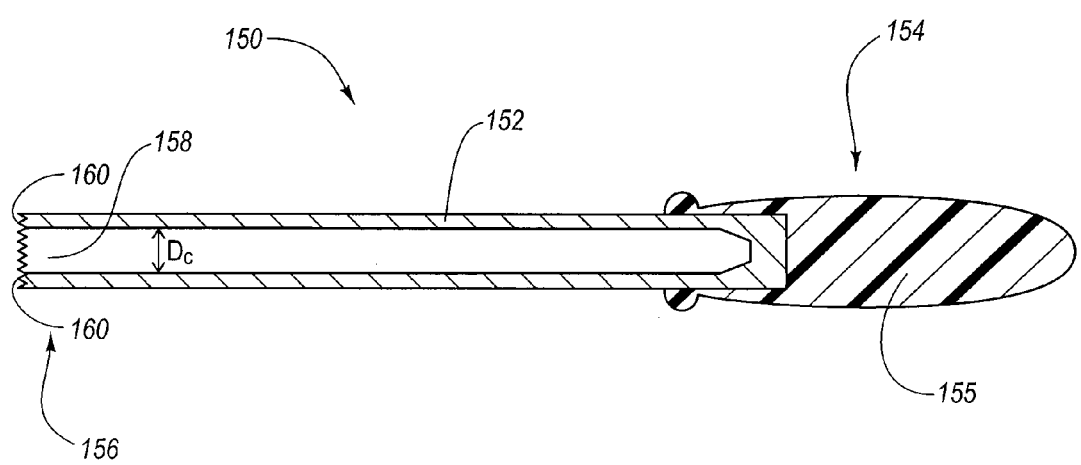
FIG. 2B is a cross-sectional view of the coring tool of FIG. 2A.

FIGS. 2A and 2B illustrate an exemplary endodontic coring tool 150 which may advantageously form part of a kit that includes the coring tool 150 and an endodontic instrument extractor tool (e.g., extractor tool 100). Coring tool 150 includes a body 152 (e.g., a hollow tube) including a proximal end 154 and a distal end 156. An interior surface of hollow body 152 defines a cavity 158 having an internal diameter $D_c$. A cutting surface 160 is advantageously disposed at distal end 156, around the circumference of hollow tube body 152. Internal diameter $D_c$ of coring tool 150 may be sized so as to correspond to internal diameter $D_1$ of extractor tool 100. In other words, in an exemplary kit, internal diameter $D_c$ of coring tool 150 may advantageously be substantially equal to internal diameter $D_1$ of extractor tool 100, such that coring tool 150 may be used to core around an end of a broken endodontic instrument, after which extractor tool 100 may be used to grip the exposed end of the broken instrument fragment so as to allow the practitioner to remove the fragment.

The body 152 of coring tool 150 may advantageously be formed of a material capable of flexing along a longitudinal axis similar to typical endodontic files used in removing material from curved root canals of a tooth. Examples of suitable materials include stainless steel, super elastic nickel-titanium alloys, and other super elastic alloy or polymer materials. Examples of suitable super elastic Ni-Ti alloys for making the coring tool include ALLOY N, ALLOY S, ALLOY C sold by MEMORY-METALLE GMBH and SE 508, sold by NITINOL DEVICES AND COMPONENTS. The flexibility of the coring tool allows the body 152 to follow the contour of the root canal, even around bends and curves. This is particularly useful where the broken endodontic instrument fragment to be retrieved is deep within a curved root canal of a tooth.

The coring tool is preferably formed of a material that can be autoclaved or otherwise sterilized so as to be reusable. Proximal end 154 includes a handle 155 or other structure that can be gripped by the practitioner or configured for insertion and engagement into a dental hand piece. In one example, handle 155 at proximal end 154 may be formed of an autoclavable plastic material (e.g., polyphenylsulfone).

Figure 3:
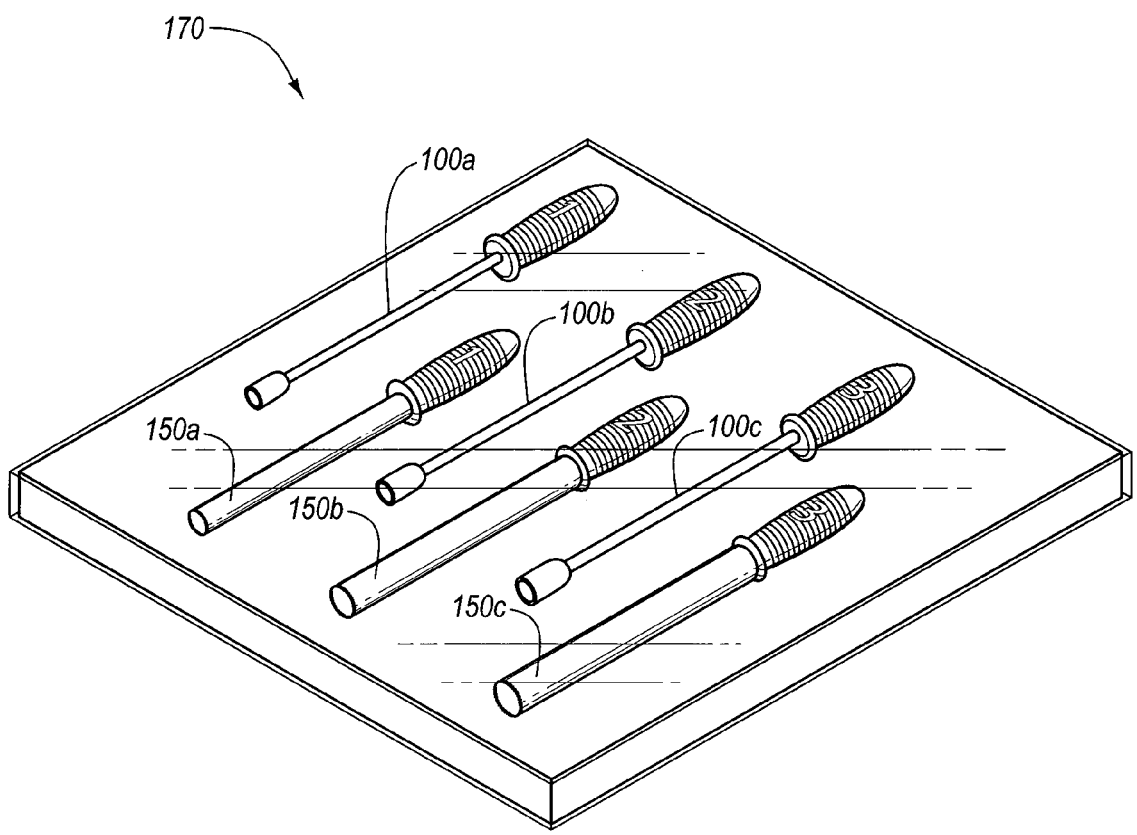
FIG. 3 is a perspective view of an exemplary kit including a plurality of differently sized endodontic extractor tools and a plurality of correspondingly sized endodontic coring tools.

Inventive kits may include multiple extractor tools and/or multiple coring tools. One such kit includes multiple extractor tools and multiple coring tools of various diameters. FIG. 3 illustrates one such exemplary kit 170 including a plurality of endodontic instrument extractor tools 100a, 100b, and 100c, and a plurality of endodontic coring tools 150a, 150b, and 150c. Endodontic extractor tools 100a, 100b, and 100c are each of a different size. In other words, they each include an internal diameter that is different from the internal diameter of the other two extractor tools. For example, endodontic extractor tool 100a may have an inside diameter of about 0.1 mm, while extractor tool 100b may have an inside diameter of about 0.5 mm, and extractor tool 100c may have an inside diameter of about 1 mm. Each inside diameter may correspond to a diameter or range of diameters of endodontic instruments typically used in the cleaning and preparation of a root canal. For example, such endodontic instruments typically have diameters ranging from about 0.03 mm to about 1.4 mm. Each extractor tool advantageously includes an internal diameter that is initially slightly greater than the diameter or range of diameters of the endodontic instrument that the extractor tool corresponds to so as to allow the broken endodontic instrument fragment to be received within the cavity defined by the internal diameter of the extractor tool.

Providing a plurality of extractor tools of different internal diameters advantageously allows a practitioner to select an appropriately sized extractor tool for use in removing a broken endodontic file or other instrument of a given diameter. The plurality of extractor tools of kit 170 allows the practitioner to choose an extractor tool for use in removing broken endodontic instrument files of a given range of diameters. Kit 170 also includes a plurality of endodontic coring tools 150a, 150b, and 150c. Similarly, each endodontic coring tool is of a different diameter size such that each internal diameter of coring tools 150a, 150b, and 150c is configured for coring around a proximal end of a broken endodontic instrument of a given sized diameter. Such a plurality of differently sized endodontic coring tools allows a practitioner to choose the smallest diameter size coring tool that will clean, core and remove tissue so as to expose the proximal end of the broken endodontic instrument. This is particularly advantageous as in the removal technique it is very helpful to remove no more of the root tissue than necessary so as to retain as much structural strength of the root as possible. As such, providing a plurality of differently sized endodontic coring tools allows the practitioner to select the smallest sized coring tool that will core around a given endodontic instrument fragment to be removed.

As illustrated, the extractor tools and coring tools may be labeled with characters (e.g., letters and/or numbers), other markings, or color coded to aid the practitioner in quickly identifying the size of any particular tool within a kit. In addition, the identification markings may be identical for extractor tools and coring tools of the same size that are configured to be used together (e.g., coring tool labeled "1" may be intended for use with the extractor tool also labeled "1"). Labeling the plurality of coring and extractor tools also allows the practitioner to easily separate and organize the plurality of coring tools should they become inter-mixed together (e.g., when several coring tools are autoclaved or otherwise sterilized together).

III. Exemplary Methods of Use

Figure 4A:
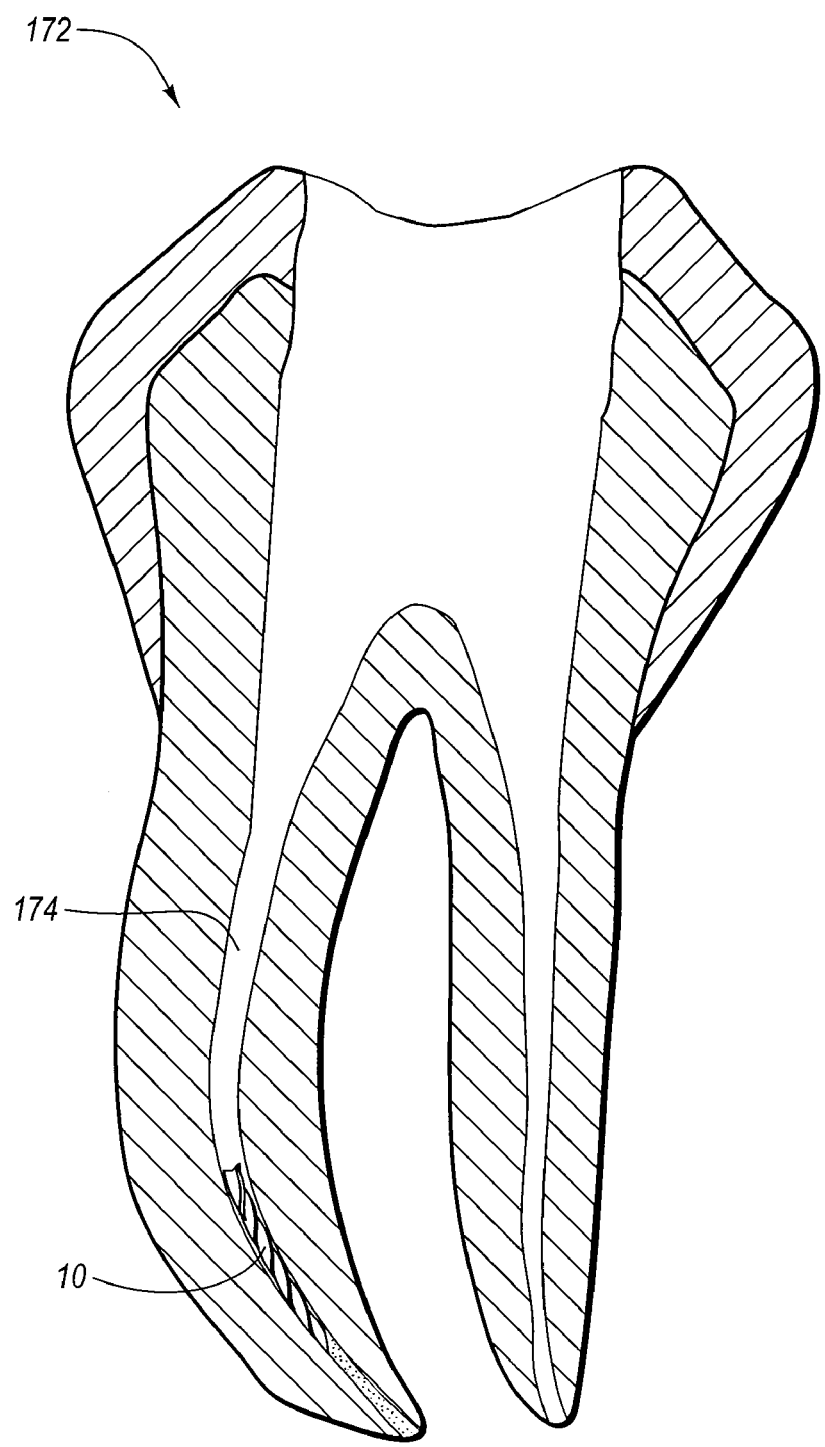
FIG. 4A shows a root canal of a tooth within which an endodontic file has broken and a fragment of the file has become lodged within the root canal.
Figure 4B:
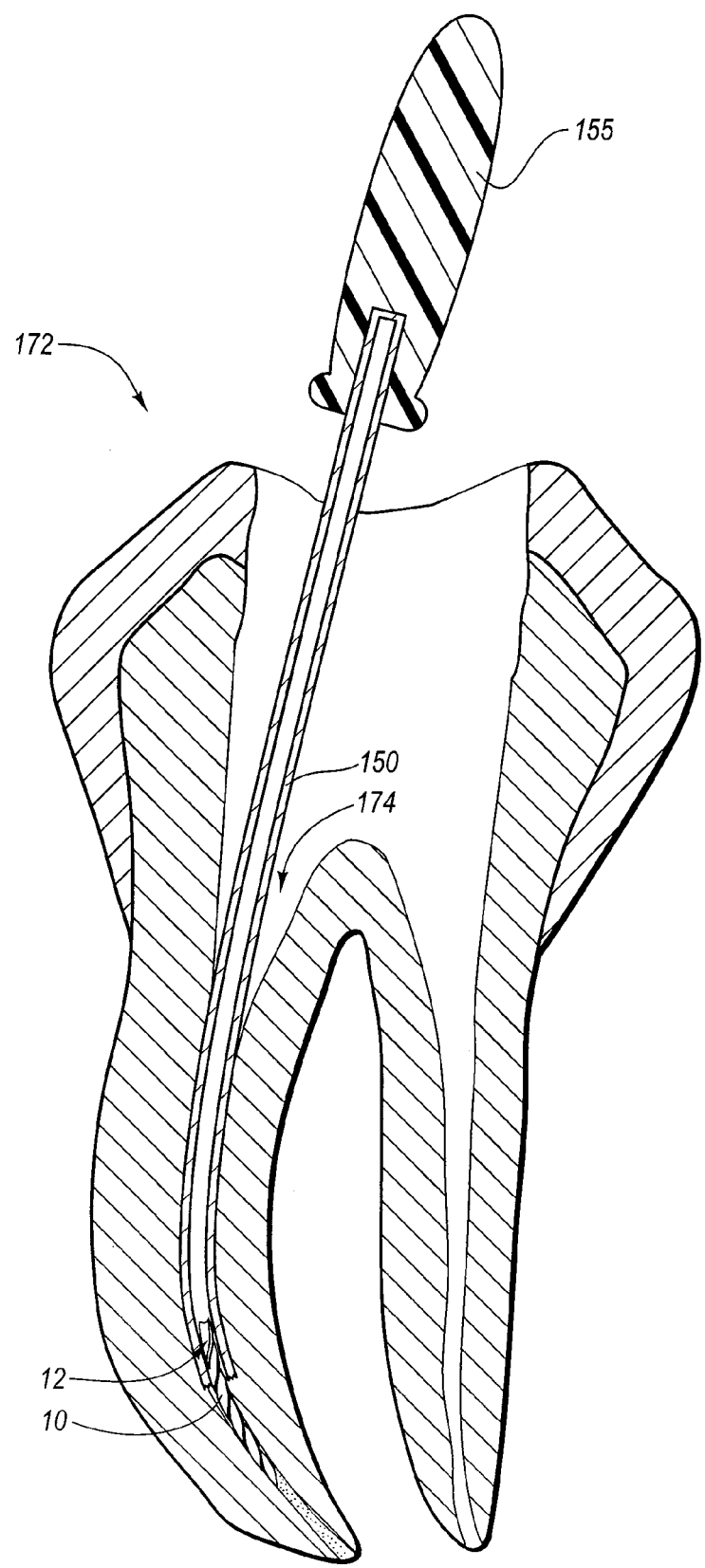
FIG. 4B shows the endodontic coring tool of FIGS. 2A-2B being used to core around and expose a proximal end of the broken endodontic file fragment of FIG. 4A.

FIG. 4A illustrates a tooth 172 having a root canal 174 within which a fragment 10 of an endodontic file has broken and become wedged within the root structure surrounding root canal 174. As seen, the broken file fragment 10 may be deep within the root canal of the tooth so as to not be easily visible or accessible to the practitioner by means of pliers or a pliers-like gripping device. Referring to FIG. 4B, an endodontic coring tool 150 is first used to core around and expose a proximal end 12 of broken endodontic file fragment 10 (e.g., by rotating and/or reciprocating coring tool 150 while applying pressure). The endodontic coring tool 150 may be selected from a kit (e.g., kit 170 of FIG. 3) based on the internal diameter of the coring tool 150. Preferably, the selected coring tool 150 has a cavity internal diameter $D_c$ (FIG. 2B) that is only slightly greater than (e.g., no more than about 5 percent greater than) the outside diameter of the proximal end of broken endodontic file fragment 10.

Figure 4C:
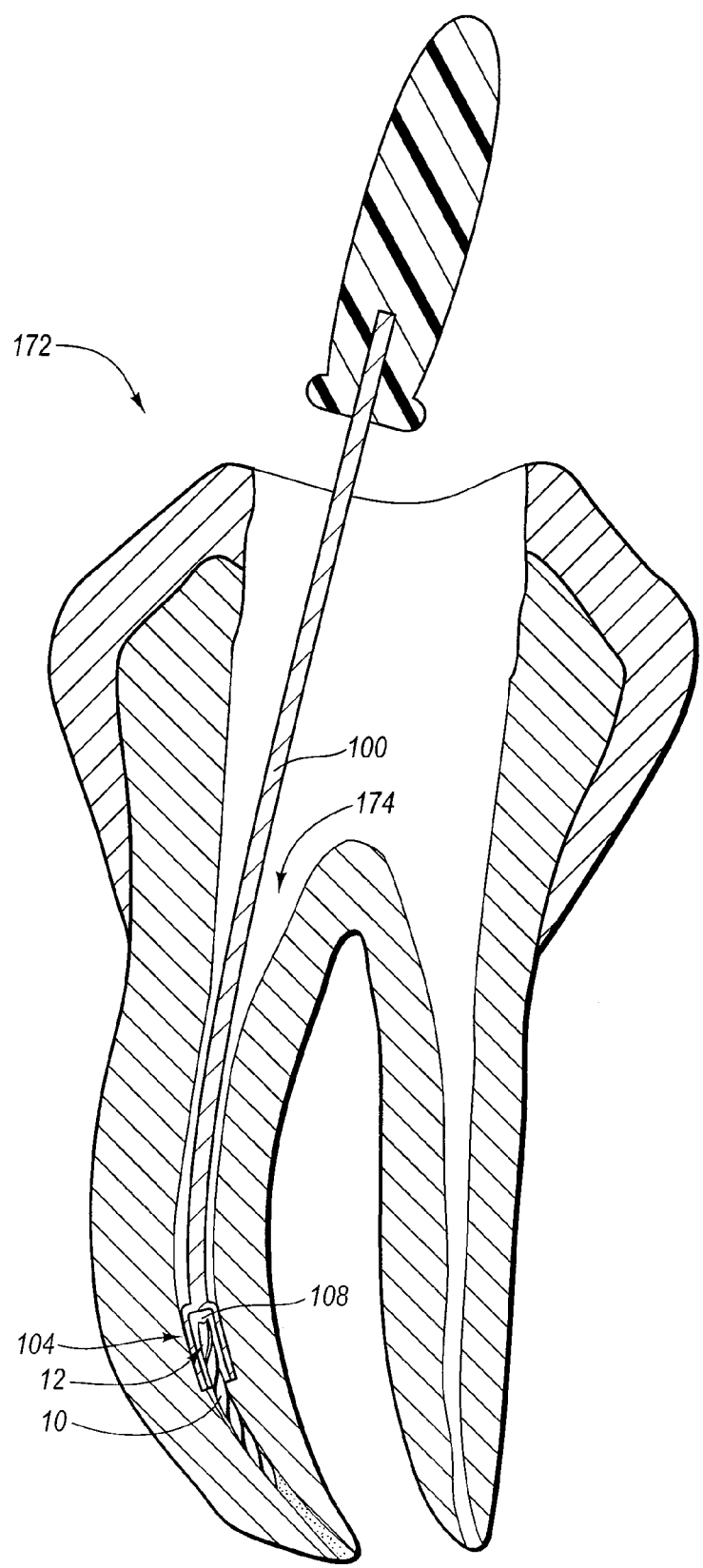
FIG. 4C shows the endodontic extractor tool inserted within the root canal of FIG. 4B so that the proximal end of the broken endodontic file fragment is received within an interior portion of the hollow gripping body of the extractor tool, the extractor tool being in an expanded configuration.

As shown in FIG. 4C, once the proximal end 12 of broken endodontic file fragment 10 has been cored around so as to expose a portion of broken file fragment 10, endodontic extractor tool 100 is inserted within root canal 174 so that the proximal end 12 of broken file fragment 10 is received within hollow interior cavity portion 108 of gripping body 104 of extractor tool 100. As seen, tool 100 is also sufficiently flexible so as to follow the contour of the root canal, even around bends and curves. The entire tool may be formed of a shape-memory nickel-titanium alloy, which has been found to exhibit sufficient flexibility, or alternatively, the elongate shaft 102 may be formed of a material similar to coring tool 150 (e.g., stainless steel, a super elastic nickel-titanium alloy, or another super elastic alloy or polymer material). Similar to coring tool 150, the hollow interior portion 108 of extractor tool 100 is initially slightly larger than the external diameter of proximal end 12 of broken endodontic file fragment 10 such that at least a portion of fragment 10 can be received within hollow interior portion 108.

Because at least the hollow gripping body 104 of extractor tool 100 is formed of a shape memory alloy or polymer that is in an expanded configuration, the extractor tool may advantageously be heated (e.g., by electrical resistance heating via electrical attachment through electrical leads (not shown) or even by the patient's body heat), which causes the shape memory alloy or polymer to return to an unexpanded configuration, reducing the inside diameter of hollow interior portion 108 so as to tightly grip the proximal portion 12 of the broken endodontic file fragment 10 that is received within interior portion 108. One contemplated method of electrical resistance heating is to provide a device connectable to a power source that includes a pair of electrical leads for connection to the shaft of the extractor tool 100. Such a device may be battery powered or may include a power cord for connection to a power outlet. In addition, the device may be included as part of the kit including an extractor tool and a coring tool as described above.

Figure 4D:
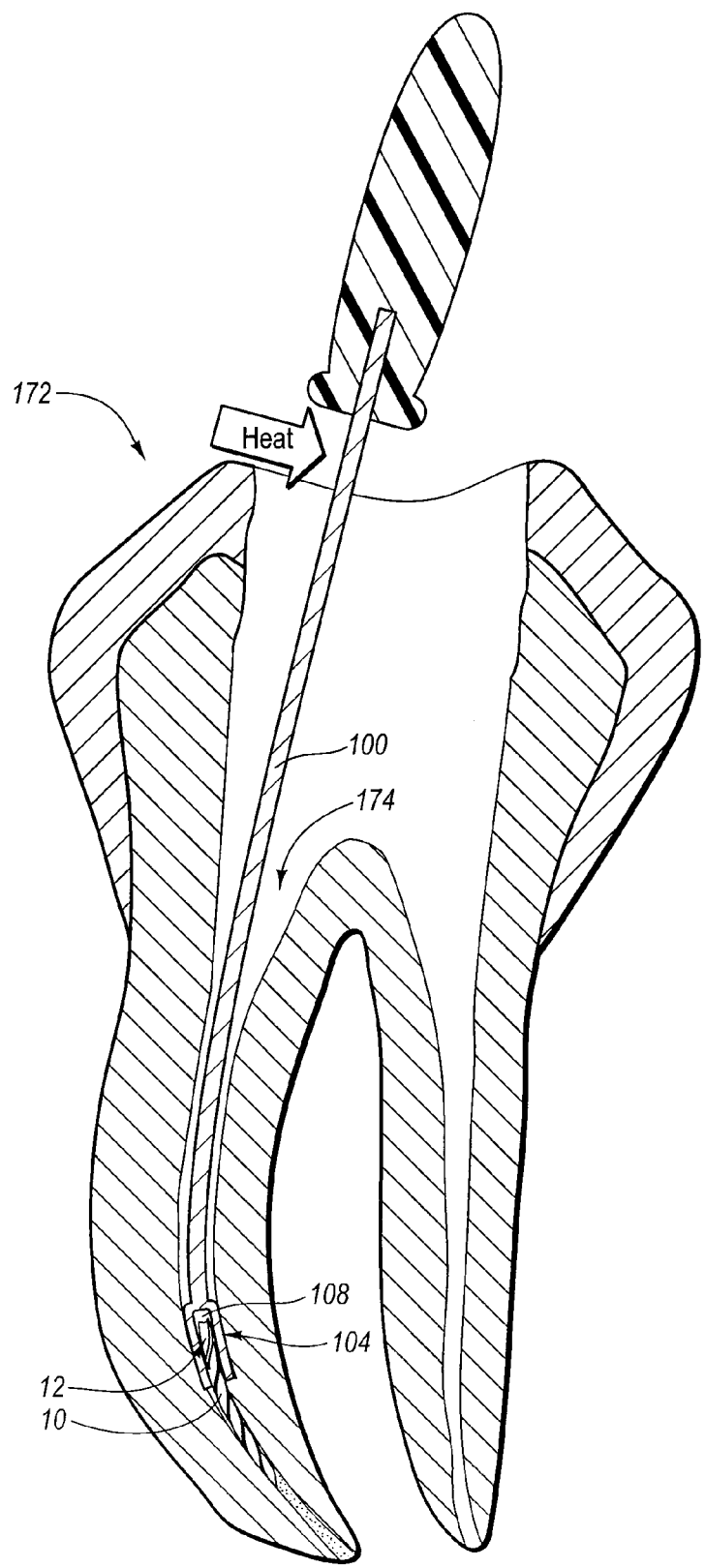
FIG. 4D shows the extractor tool having been heated so as to assume an un-expanded configuration such that the proximal end of the broken endodontic file fragment is tightly gripped within the hollow gripping body of the extractor tool.

The hollow gripping body 104 of the extractor tool 100 may be heated to any suitable temperature range greater than room temperature (FIG. 4D). In one embodiment, the shape memory alloy or polymer is heated simply by exposure to the body heat of the patient (e.g., to about 100° F.). In a preferred embodiment, the shape memory alloy or polymer must be heated to a somewhat higher threshold temperature so as to cause it to return to an unexpanded configuration. For example, it may be heated to a temperature between about 110° F. and about 200° F., more preferably between about 130° F. and about 180° F., and most preferably between about 135° F. and about 160° F. Such a configuration sets the minimum threshold trigger temperature at which the shape memory alloy or polymer returns to an unexpanded configuration above typical storage and/or shipping temperatures, which reduces the possibility that the extractor tool will reach the trigger temperature prematurely (e.g., during storage and/or shipping), which would result in waste as the extractor tool is typically not intended for reuse once it has been heated above the minimum threshold temperature at which the hollow gripping body 104 returns to an unexpanded configuration.

Figure 4E:
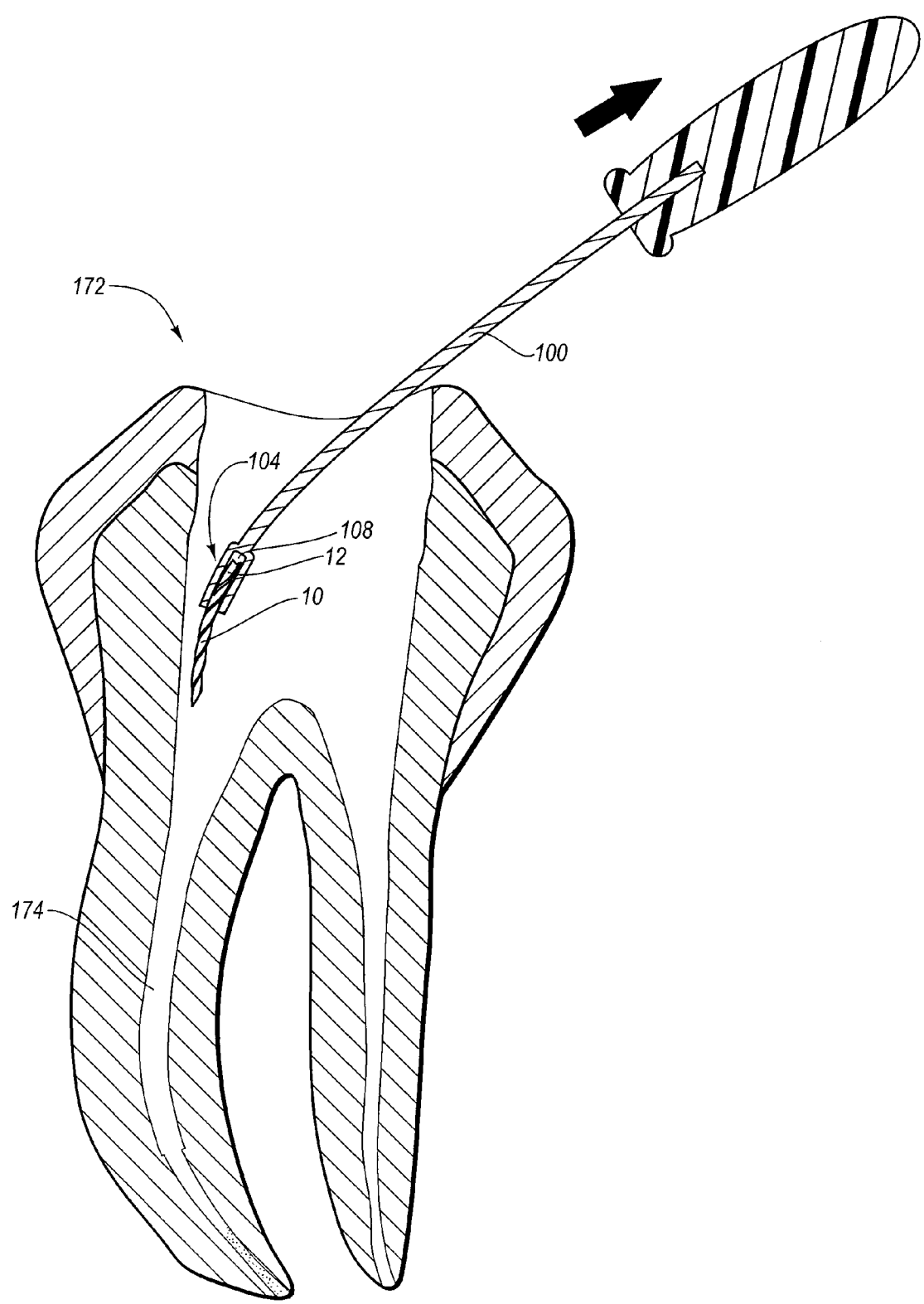
FIG. 4E shows the extractor tool and broken endodontic file fragment being removed together from the root canal of the tooth.

Because of the tight grip upon proximal end 12, the practitioner is then able to remove extractor tool 100 and broken endodontic file fragment 10 together from root canal 174 (FIG. 4E). Because the broken endodontic file fragment 10 is likely wedged within the hard root structure surrounding root canal 174, the practitioner may be required to twist the extractor tool and endodontic file fragment in an opposite direction as was used when the broken file became wedged and broken in order to remove it from the root canal 174 of tooth 172. The extractor tool 100 and file fragment 10 may simply be discarded, and the practitioner may complete preparation, filling, and sealing of the root canal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An endodontic instrument extractor tool for removing a broken endodontic instrument that has become lodged within a root canal of a tooth, comprising:
   an elongate shaft having a proximal end and a distal end, at least the distal end of the elongate shaft being insertable into root canal of a tooth, the elongate shaft having a length so that the proximal end extends outside the tooth when the distal end is positioned within a root canal of a tooth; and
   gripping means formed of a shape memory material, disposed at the distal end of the elongate shaft, for gripping a portion of a broken endodontic instrument that has become lodged within a root canal of a tooth by causing the gripping means to shrink around at least a portion of the broken endodontic instrument in response to application of heat energy to the gripping means.

2. An endodontic instrument extractor tool as recited in claim 1, wherein the gripping means comprises a hollow body having an outer wall defining a hollow interior portion and.

3. An endodontic instrument extractor tool as recited in claim 2, wherein the outer wall is flared.

4. An endodontic instrument extractor tool as recited in claim 2, wherein the outer wall of the hollow body is substantially cylindrical.

5. An endodontic instrument extractor tool as recited in claim 2, wherein the outer wall of the hollow body has a substantially smooth interior surface for contacting the broken endodontic file.

6. An endodontic instrument extractor tool as recited in claim 2, wherein the outer wall of the hollow body has a roughened interior surface for contacting the broken endodontic file.

7. An endodontic instrument extractor tool as recited in claim 2, wherein the outer wall of the hollow body has a diameter that exceeds the diameter of the distal end of the elongate shaft.

8. An endodontic instrument extractor tool as recited in claim 2, wherein the inside diameter of the hollow interior portion of the hollow body is initially between about 0.03 mm and about 1.75 mm.

9. An endodontic instrument extractor tool as recited in claim 2, wherein the outer wall of the hollow body comprises a nickel-titanium alloy having shape memory.

10. An endodontic instrument extractor tool as recited in claim 9, wherein the nickel-titanium alloy comprises at least about 40% titanium.

11. An endodontic instrument extractor tool as recited in claim 10, wherein the balance of the nickel-titanium alloy consists essentially of nickel.

12. An endodontic instrument extractor tool as recited in claim 10, wherein the balance of the nickel-titanium alloy further comprises nickel and at least one of copper and/or niobium.

13. An endodontic instrument extractor tool as recited in claim 9, wherein the nickel-titanium alloy comprises at least about 50% titanium.

14. An endodontic instrument extractor tool as recited in claim 1, further comprising an enlarged gripping handle at the proximal end of the elongate shaft.

15. An endodontic instrument extractor tool for removing a broken endodontic instrument that has become lodged within a root canal of a tooth, comprising:
   an elongate shaft having a proximal end and a distal end, at least the distal end of the elongate shaft being insertable into root canal of a tooth, the elongate shaft having a length so that the proximal end extends outside the tooth when the distal end is positioned within a root canal of a tooth; and
   a hollow gripping body disposed at a distal end of the elongate shaft having an outer wall defining a hollow interior portion having an initial diameter that is greater than an outer cross-sectional dimension of a broken endodontic instrument to be extracted, the hollow body comprising a material having shape memory such that, upon heating to above a minimum threshold temperature, the hollow body shrinks in size in order for the hollow interior portion to have reduced diameter so as to thereby grip the broken endodontic instrument within the hollow interior portion.

16. An endodontic instrument extractor tool as recited in claim 15, wherein the outer wall of the hollow body comprises a nickel-titanium alloy having shape memory.

17. An endodontic instrument extractor tool as recited in claim 1, wherein the endodontic instrument extractor tool is included as part of a kit that also includes an endodontic coring tool comprising a hollow tube and a cutting surface at a distal end of the hollow tube for coring around a fragment of a broken endodontic instrument.

18. A kit as recited in claim 17, further comprising a plurality of endodontic instrument extractor tools and endodontic coring tools of different sizes in order to facilitate extraction of differently-sized broken endodontic instruments that may individually become lodged in a root canal of a tool.

19. A method of removing a fragment of a broken endodontic instrument that has become lodged within a root canal of a tooth during an endodontic procedure, comprising:
- selecting an endodontic instrument extractor tool as defined in claim 1;
- inserting the gripping means and distal end of the elongate shaft of the endodontic instrument extractor tool into a root canal of a tooth in order for the gripping means to engage an end of a broken endodontic instrument lodged in the root canal;
- heating the gripping means in order to cause the gripping means to securely grip the end of a broken endodontic instrument; and
- removing the broken endodontic instrument from the root canal.

20. A method as recited in claim 19, further comprising coring around an end of the broken endodontic instrument prior to inserting the endodontic instrument extractor tool into the root canal.

21. A method as recited in claim 19, wherein heating the gripping means is accomplished by electrical resistance heating.

22. A method as recited in claim 19, wherein heating the gripping means is accomplished by exposure to body heat.

23. A method as recited in claim 19, wherein the gripping means is heated to a temperature between about 110° F. and about 200° F.

24. A method as recited in claim 19, wherein the gripping means is heated to a temperature between about 130° F. and about 180° F.

25. A method as recited in claim 19, wherein the gripping means is heated to a temperature between about 135° F. and about 160° F.

* * * * *

UNITED STATES PATENT AND TRADEMARK OFFICE
CERTIFICATE OF CORRECTION

PATENT NO. : 7,367,804 B2  
APPLICATION NO. : 11/467418  
DATED : May 6, 2008  
INVENTOR(S) : Paul Lewis Page 1 of 1

It is certified that error appears in the above-identified patent and that said Letters Patent is hereby corrected as shown below:

Column 3
Line 44, change "increased" to --increases--

Column 4
Line 15, change "1A-1B" to --1A-1C--
Line 33, change "un-expanded" to --unexpanded--

Column 9
Line 65, change "and." to --.--

Column 10
Line 7, change "file" to --instrument--
Line 11, change "file" to --instrument--

Signed and Sealed this

Tenth Day of February, 2009

JOHN DOLL
*Acting Director of the United States Patent and Trademark Office*